US006656120B2

(12) United States Patent
Lee et al.

(10) Patent No.: US 6,656,120 B2

(45) Date of Patent: Dec. 2, 2003

(54) ULTRASOUND IMAGING SYSTEM USING KNOWLEDGE-BASED IMAGE ADJUSTING DEVICE

(75) Inventors: Seong Woo Lee, Seoul (KR); Young Seuk Song, Sould (KR); Jung Wha Kim, Seoul (KR)

(73) Assignee: Madison Co., LTD, Kangwon-Do (KR)

( * ) Notice: Subject to any disclaimer, the term of this patent is extended or adjusted under 35 U.S.C. 154(b) by 0 days.

(21) Appl. No.: 10/295,741

(22) Filed: Nov. 15, 2002

(65) Prior Publication Data

US 2003/0097065 A1 May 22, 2003

(30) Foreign Application Priority Data

Nov. 16, 2001 (KR) ................................ 10-2001-0071275

(51) Int. Cl.$^{7}$ ............................ A61B 8/00; G06F 17/60

(52) U.S. Cl. ............................................ 600/437; 705/3

(58) Field of Search ................................ 600/437, 443, 600/449; 705/3, 2; 382/128, 130–132

(56) References Cited

U.S. PATENT DOCUMENTS 5,295,485 A * 3/1994 Shinomura et al. ......... 600/443
5,603,323 A * 2/1997 Pflugrath et al. ........... 600/437
5,891,035 A * 4/1999 Wood et al. ................ 600/437
5,897,498 A * 4/1999 Canfield et al. ............ 600/437
6,506,155 B2 * 1/2003 Sluis .......................... 600/437
2002/0194029 A1 * 12/2002 Guan et al. .................... 705/3

* cited by examiner

*Primary Examiner*—Marvin M. Lateef
*Assistant Examiner*—Ruby Jain
(74) *Attorney, Agent, or Firm*—Thelen Reid & Priest LLP; David B. Ritchie

(57) ABSTRACT

An ultrasound imaging system using a knowledge-based image adjusting device, which enables to obtain the optimal ultrasound image by automatically adjusting image parameters on the basis of pre-stored patient information so that operating procedures required of a system operator are reduced. The ultrasound imaging system comprises a patient information recording medium; a reference image database for storing reference image parameters; a similarity calculation unit for comparing patient information and corresponding reference image parameters and determining the parameter with the highest similarity; and an image adjusting block for selecting a type of probe and automatically adjusting image settings of the selected probe. The ultrasound imaging system further comprises a user input device for inputting and adjusting degrees of freedom parameters.

9 Claims, 4 Drawing Sheets

200
20a
20b
Feature Parameter DB
Image Parameter DB
20
40a
10
Patient Information Recording Medium
Similarity Calculation Unit
30
Probe Selection Unit
40
Image Adjusting Unit
To Display
40b
User Input Device
50

100
20a
20b
20
Feature Parameter DB
Image Parameter DB
10
Patient Information Recording Medium
Similarity Calculation Unit
30
40a
Probe Selection Unit
40
Image Adjusting Unit
40b
To Display

Fig. 2

| Diagnostic Items | Feature Parameters | Criteria |
|---|---|---|
| Abdomen | Fatty, Standard(normal), Thin, Pediatric, Kidney, Appendix, Uterus | Each organ within the abdomenial region |
| OB | Early(within 12wks), 1st (12~24wks), 2nd (24~32wks), 3rd(32wks and more), Fetal echo | Generally divided in three steeps by the fetal developement and growth |
| Small part | Thyroid, Breast, Extremity, Vascular, Appendix, Colon | Divided by superficial parts of human body |
| Cardiac (adult) | Parasternal long axis, Parasternal short axis, Apical 4 chamber, Apical 2 chamber | Four basic views for examining cardiac disease |
| GYN | Uterus, Ovary, Early fetus, Prostate | Divided by each organ in male/female lower abdomen;early fetus presents early pregnancy examinated by using transvaginal probe |
| ETC | . . . | . . . |

Fig. 3

| Feature Parameters | Image Parameters |
| --- | --- |
| Fatty | Gain(1), Contrast(1), Edge(1),... |
| Tyroid | Gain(2), Contrast(2), Edge(2),... |
| Feta Echo | Gain(3), Contrast(3), Edge(3),... |
| ⋮ | ⋮ |

200
10
Patient Information Recording Medium
20
20a
Feature Parameter DB
20b
Image Parameter DB
30
Similarity Calculation Unit
40
40a
Probe Selection Unit
40b
Image Adjusting Unit
To Display
50
User Input Device

ULTRASOUND IMAGING SYSTEM USING KNOWLEDGE-BASED IMAGE ADJUSTING DEVICE

FIELD OF THE INVENTION

The present invention relates to an ultrasound imaging system, and more particularly, to an ultrasound imaging system using a knowledge-based image adjusting device.

BACKGROUND OF THE INVENTION

In general, to provide accurate diagnosis using an ultrasound imaging system, optimal ultrasound images showing the diagnostic region of the patient must be obtained. To obtain the optimal ultrasound images, a system operator selects a probe suitable for patients' conditions and diagnostic regions, and finely adjusts image parameters, such as brightness, resolution, and contrast. Conventionally, selecting a suitable probe and adjusting image parameters have been performed manually by the system operator rather than automatically by the ultrasound imaging system.

In a conventional ultrasound imaging system, obtaining optimal ultrasound images is highly dependent on the personal ability of the system operator, e.g., the operator's experience and skill in handling the system. The procedures for obtaining optimal ultrasound images are highly complicated. System operators, who usually operate the system to diagnose a great number of different patients per day, thus suffer from excessive work fatigue. Also the complicated adjustment procedures increase the time required to diagnose patients.

Some system operators operate the system to diagnose every patient under preset system conditions without performing the above-mentioned fine adjustments. Thus, optimal ultrasound images for the respective patients are not obtained, which may result in less than optimal diagnoses. Therefore, a system is needed that minimizes the above-mentioned procedures performed manually by a system operator without degrading the quality of ultrasound images, in order to obtain ultrasound images optimized for the particular patient's condition.

Furthermore, conventional ultrasound imaging systems employ a user input device, which is used by a system operator for entering image parameters one-by-one. This input manner is very inconvenient for the system operator to operate three-dimensional ultrasound imaging system. As the number of image parameters to be entered through the user input device increases, the inconvenience is one of the major shortcomings obstructing full system performance. Accordingly, a user input device is needed that is capable of providing convenience in use and reducing preparation time required to diagnose patients, by allowing system operators to enter various parameters at once, the various parameters being necessary to the rotation and movement of three-dimensional ultrasound images in rectangular coordinates, angular coordinates, and spherical coordinates.

SUMMARY OF THE INVENTION

It is, therefore, an objective of the present invention to provide an ultrasound imaging system using a knowledge-based image adjusting device, capable of obtaining optimal ultrasound images for patients by automatically adjusting image parameters on the basis of pre-stored patient information and reducing manual operation procedures of a system operator.

Also, it is another objective of the present invention to provide an ultrasound imaging system employing a user input device capable of providing convenience in use and reducing preparation time required to diagnose patients, by allowing system operators to operate various input devices at once.

In accordance with a first embodiment of the present invention, an ultrasound imaging system using a knowledge-based image adjusting device for producing ultrasound images, comprising: a patient information database for storing patient information; a reference image database for storing reference image parameters; a similarity calculation unit, in communication with the patient information database and the reference image database, which compares patient information and corresponding reference image parameters, and determines a parameter with the highest similarity; and an image adjusting block, in communication with the similarity calculation unit, which selects a type of probe and automatically adjusts image settings of the selected probe based on the parameter with the highest similarity.

Also, in accordance with a second embodiment of the present invention, an ultrasound imaging system using a knowledge-based image adjusting device for producing ultrasound images, comprising: a patient information database for storing patient information; a reference image database for storing reference image parameters; a similarity calculation unit, in communication with the patient information database and the reference image database, which compares patient information and corresponding reference image parameters, and determines a parameter with the highest similarity; an image adjusting block, in communication with the similarity calculation unit, which selects a type of probe and automatically adjusts image settings of the selected probe based on the parameter with the highest similarity; and a user input device, in communication with the similarity unit, for inputting and adjusting degrees of freedom parameters.

BRIEF DESCRIPTION OF DRAWINGS

The above and other objects and features of the present invention will become apparent from the following description of the embodiments given in conjunction with the accompanying drawings.

FIG. 2 is an example of the plurality of feature parameters stored in a feature parameter database shown in FIG. 1.

FIG. 3 is an example of the plurality of image parameters stored in an image parameter database shown in FIG. 1.

DETAILED DESCRIPTION OF THE PRESENT INVENTION

Figure 1:
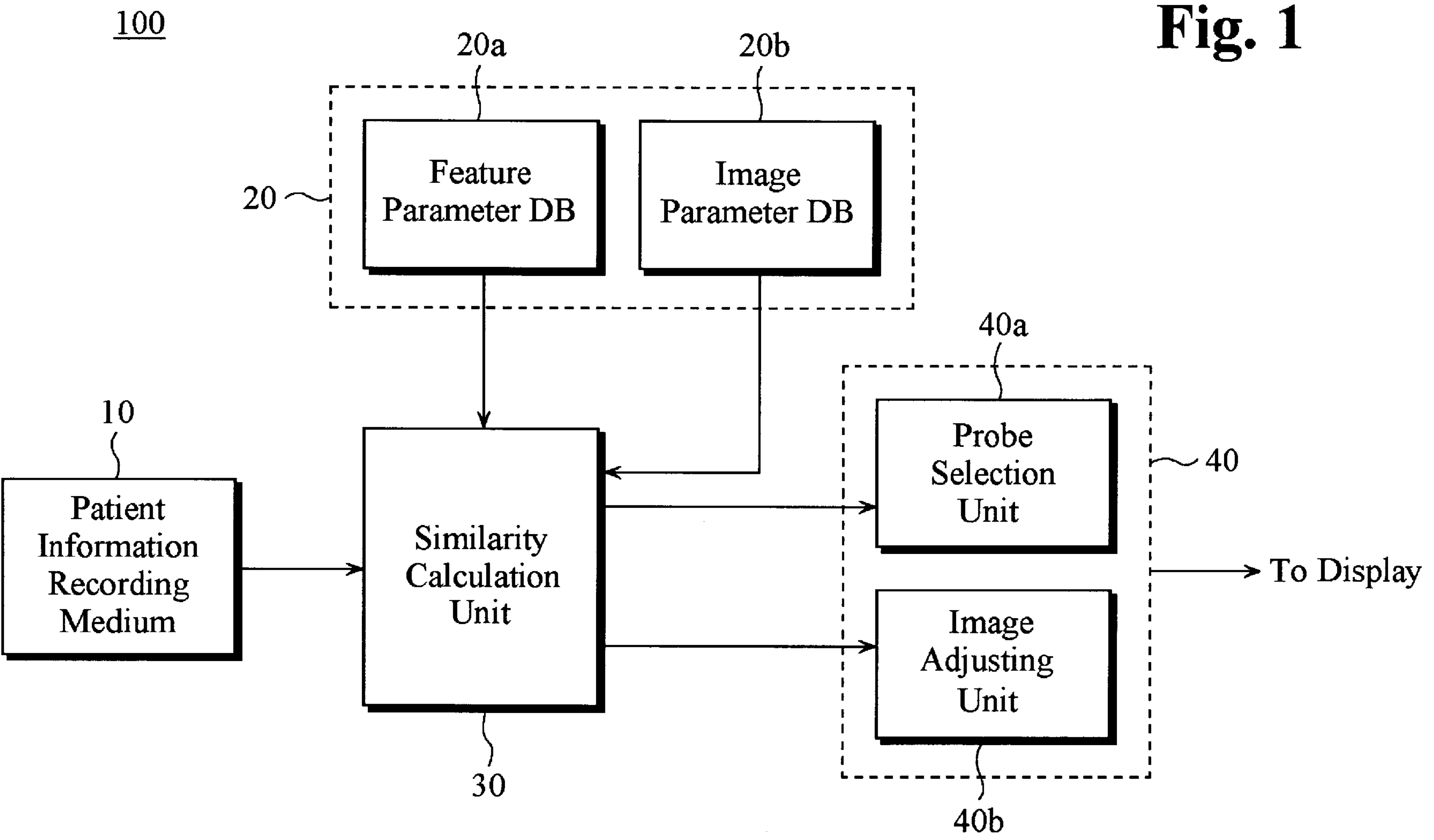
FIG. 1 is a block diagram of an ultrasound imaging system in accordance with a first embodiment of the present invention.

Referring to FIG. 1, an ultrasound imaging system in accordance with a first embodiment of the present invention is shown. Ultrasound imaging system 100 comprises a patient information recording medium 10, a reference image parameter database (DB) 20, a similarity calculation unit 30, and an image adjusting block 40. Patient information recording medium 10 stores patient information such as physical conditions, records of diseases, and medical history of a patient and is implemented as a health card or a work-list.

The health card is capable of storing predetermined amounts of patient information, which can be read through a device, e.g., a card reader (not shown). The health card can preferably be used as patient information recording medium 10 since there is no need to establish the network infrastructure within a hospital.

The work-list is a list of records of a patient's physical conditions, diseases, medical history, diagnostic images, etc. that is kept by hospitals. Where patient information recording medium 10 is implemented as a work-list, ultrasound imaging system 100 must be connected to the network infrastructure in the hospital. Patient information can be stored in a central storage unit of the hospital and then withdrawn as a work-list.

Reference image parameter DB 20 is comprised of feature parameter DB 20*a* and image parameter DB 20*b*, and stores reference parameters such as feature parameters and image parameters for each of diagnostic items, which are pre-classified according to patients' conditions, diseases, etc. Referring to FIG. 2, feature parameter DB 20*a* stores a plurality of feature parameters corresponding to each of the diagnostic items, which are classified by diagnostic regions and their corresponding criteria. Referring to FIG. 3, image parameter DB 20*b* stores a plurality of image parameters corresponding to each of the feature parameters. The image parameters include brightness, contrast, gain, edge strength, receiving/transmitting frequency, and ultrasound average velocity.

Referring back to FIG. 1, similarity calculation unit 30 is connected to patient information recording medium 10, feature parameter DB 20*a*, and image adjusting block 40. Similarity calculation unit 30 extracts information corresponding to the feature parameters stored in feature parameter DB 20*a* from the patient information, which are transferred from patient information recording medium 10. Similarity calculation unit 30 compares the extracted information with the feature parameters to calculate similarities therebetween. Similarity calculation unit 30 extracts one feature parameter having the highest similarity among the calculated similarities and selects a diagnostic item including the extracted feature parameter from feature parameter DB 20*a*. Thereafter, similarity calculation unit 30 extracts feature parameters included in the selected diagnostic item and retrieves image parameters corresponding to the extracted feature parameters from image parameter DB 20*b*. The selected diagnostic item and the retrieved image parameters are transmitted from similarity calculation unit 30 to image adjusting block 40.

Image adjusting block 40 is comprised of probe selection unit 40*a* and image adjusting unit 40*b* and connected to similarity calculation unit 30. Probe selection unit 40*a* receives the selected diagnostic item from similarity calculation unit 30 to select a probe suitable for the selected diagnostic item. A signal device (not shown) notifies the system operator of information from the selected probe. Image adjusting unit 40*b* receives the retrieved image parameters from similarity calculation unit 30 to automatically adjust ultrasound imaging system 100. For example, image adjusting unit 40*b* automatically adjusts the image settings of ultrasound imaging system 100 with respect to ultrasound images to be obtained through the selected probe, based on the retrieved image parameters, such as gain, contrast, and edge strength. The adjusted image settings are transmitted from image adjusting unit 40*b* to a display unit (not shown).

Figure 4:
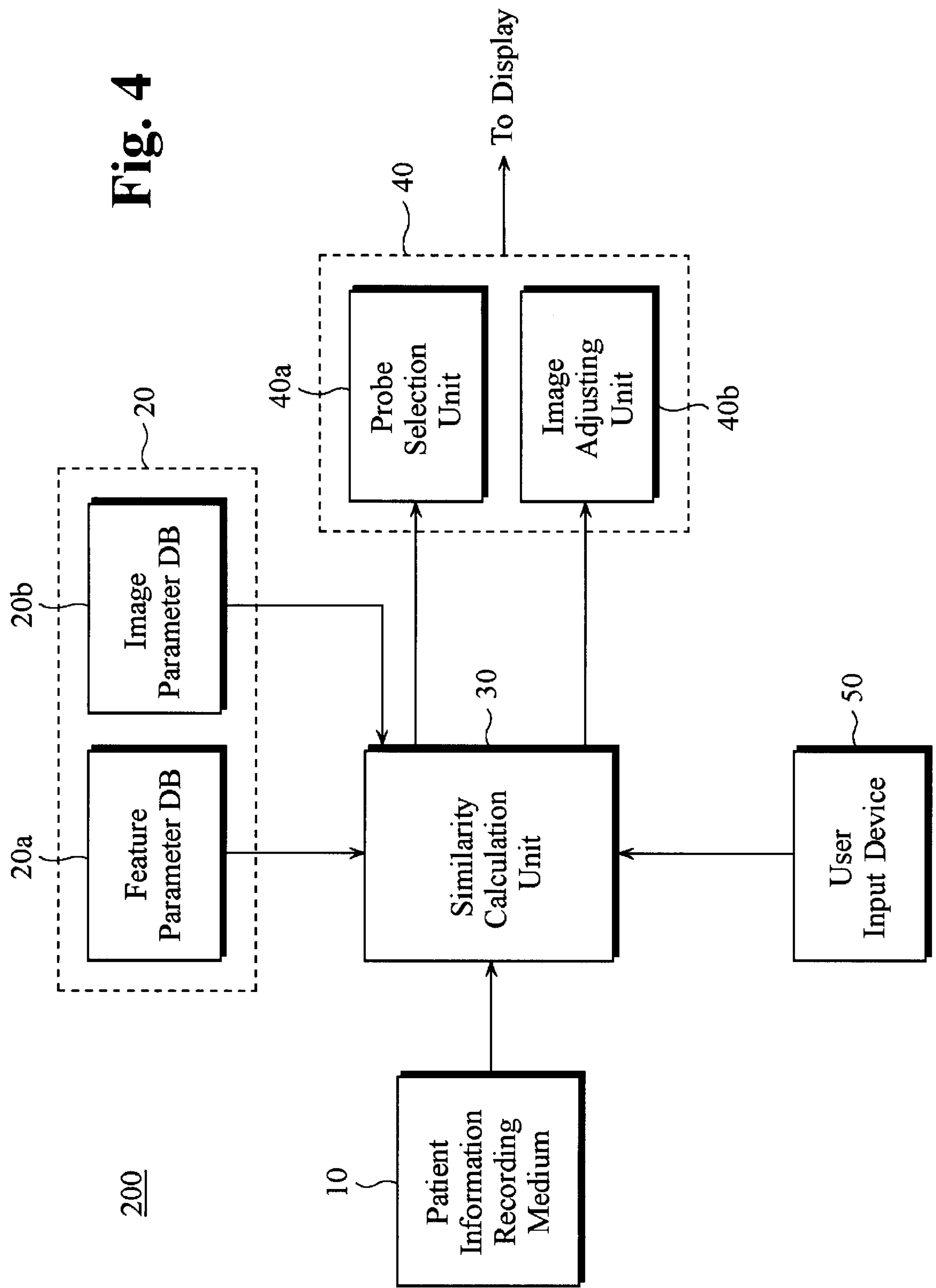
FIG. 4 is a block diagram of an ultrasound imaging system employing a user input device in accordance with a second embodiment of the present invention.

Referring to FIG. 4, a block diagram of an ultrasound imaging system employing a user input device in accordance with a second embodiment of the present invention is shown. Ultrasound imaging system 200 comprises a patient information recording medium 10, a reference image parameter DB 20, a similarity calculation unit 30, and an image adjusting block 40, similar to those in ultrasound imaging system 100 shown in FIG. 1, and further a comprises user input device 50. For convenience, detailed descriptions of the elements with the same reference numerals as those in FIG. 1 are omitted.

User input device 50 is used to optimize the ultrasound images obtained by the above-mentioned embodiment of the present invention. User input device 50 is used when the system operator needs to input and adjust parameters—the parameters being necessary to the rotation and movement of ultrasound images in rectangular coordinates, angular coordinates, and spherical coordinates. User input device 50 is capable of inputting and processing various degrees of freedom for the rotation and movement of ultrasound images in rectangular coordinates, angular coordinates, and spherical coordinates. For example user input device 50 may be a touch screen, wherein parameters are inputted by a hand or a pen (stylus).

If input and adjustment of parameters is needed, the system operator enters the parameters using user input device 50. As the touch screen processes data inputted on its screen by a hand or a pen, it can receive the system operator's handwriting. Such that, it can be also used as a medical certificate by accompanying the system operator's signature after inputting opinion according to ultrasound image diagnostic results and raises the reliability of medical opinion. As described above, user input device 50 provides convenience and speedy system operation for system operators, as well as comfortable and reliable diagnoses to patients, due to the reduction in preparation and diagnostic time.

In accordance with the present invention, system operation procedures required of a system operator is dramatically reduced by automatically selecting a probe needed for the diagnosis of patients and adjusting parameters related to ultrasound images depending on diagnostic regions and patient conditions. Therefore, the system operator may easily operate the ultrasound imaging system with reduced preparation and diagnostic time. Also, the system operator is provided with ultrasound images optimized by the automatic adjustment of image parameters, which are suitable for the individual patient's condition, and able to make more accurate diagnoses. Further, with user-oriented input devices, such as an input device having various degrees of freedom and a touch screen, one can use the ultrasound imaging system of the present invention with more convenience.

While particular embodiments of the present invention have been shown and described, it will be obvious to those skilled in the art that changes and modifications may be made without departing from this invention in its broader aspects and, therefore, the aim in the appended claims is to cover all such changes and modifications, as fall within the true spirit and scope of this invention.

What is claimed is:

1. An ultrasound imaging system using a knowledge-based image adjusting device for producing ultrasound images, comprising:

a patient information database for storing patient information;

a reference image database for storing reference image parameters;

a similarity calculation unit, in communication with the patient information database and the reference image database, which compares patient information and corresponding reference image parameters, and determines a parameter with the highest similarity; and an image adjusting block, in communication with the similarity calculation unit, which selects a type of probe and automatically adjusts image settings of the selected probe based on the parameter with the highest similarity.

2. The ultrasound imaging system of claim 1, wherein the patient information database is stored on a health card.

3. The ultrasound imaging system of claim 1, wherein the patient information database is stored as a work-list.

4. The ultrasound imaging system of claim 2 or 3, wherein the patient information comprises a patient's physical condition, record of disease, or medical history.

5. The ultrasound imaging system of claim 1, wherein the reference image database further comprises:

a feature parameter database for storing a plurality of feature parameters for each of diagnostic items that are classified by patients' physical conditions and diseases; and an image parameter database for storing a plurality of image parameters corresponding to the respective feature parameters.

6. The ultrasound imaging system of claim 5, wherein the image parameters stored on said image parameter database include brightness, contrast, gain, edge strength, receiving/transmitting frequency, and ultrasound average velocity.

7. The ultrasound imaging system of claim 1, further comprising:

a user input device, in communication with the similarity calculation unit, for inputting and adjusting degrees of freedom parameters.

8. The ultrasound imaging system of claim 7, wherein the degrees of freedom parameters are related to rotation and movement of ultrasound images in rectangular coordinates, angular coordinates, or spherical coordinates.

9. The ultrasound imaging system of claim 7, wherein the user input device further comprises a touch screen.

* * * * *

UNITED STATES PATENT AND TRADEMARK OFFICE

CERTIFICATE OF CORRECTION

PATENT NO. : 6,656,120 B2
DATED : December 2, 2003
INVENTOR(S) : Seong Woo Lee, Young Seuk Song and Jung Wha Kim It is certified that error appears in the above-identified patent and that said Letters Patent is hereby corrected as shown below:

Title page,
Item [73], Assignee, replace "Madison" with -- Medsion --.

Signed and Sealed this

Sixth Day of April, 2004

JON W. DUDAS
*Acting Director of the United States Patent and Trademark Office*

UNITED STATES PATENT AND TRADEMARK OFFICE

CERTIFICATE OF CORRECTION

PATENT NO. : 6,656,120 B2
APPLICATION NO. : 10/295741
DATED : December 2, 2003
INVENTOR(S) : Seong Woo Lee, Young Seuk Song and Jung Wha Kim It is certified that error appears in the above-identified patent and that said Letters Patent is hereby corrected as shown below:

Title page,
Item [73], Assignee, replace "Madison" with -- Medison --.

This certificate supersedes the Certificate of Correction issued April 6, 2004.

Signed and Sealed this

Twenty-eighth Day of October, 2008

JON W. DUDAS
*Director of the United States Patent and Trademark Office*